(12) United States Patent
Kim et al.

(10) Patent No.: US 8,114,987 B2
(45) Date of Patent: Feb. 14, 2012

(54) PREPARATION METHOD OF 2-DEOXY-L-RIBOSE

(75) Inventors: Kyung-Il Kim, Gyeonggi-do (KR); Seung-Bum Ha, Seoul (KR); Jae-Hoon Jeon, Daejeon (KR); Soon-Jeong Kwon, Gyeonggi-do (KR); Yong-Tae Kim, Daejeon (KR); Ji-Suk Yun, Gyeongsangbuk-do (KR)

(73) Assignee: Samchully Pharm. Co. Ltd., Seoul (KR)

( * ) Notice: Subject to any disclaimer, the term of this patent is extended or adjusted under 35 U.S.C. 154(b) by 312 days.

(21) Appl. No.: 12/312,889

(22) PCT Filed: Oct. 24, 2007

(86) PCT No.: PCT/KR2007/005244
§ 371 (c)(1),
(2), (4) Date: May 29, 2009

(87) PCT Pub. No.: WO2008/069440
PCT Pub. Date: Jun. 12, 2008

(65) Prior Publication Data
US 2009/0292117 A1 Nov. 26, 2009

(30) Foreign Application Priority Data
Dec. 6, 2006 (KR) .................. 10-2006-0122752

(51) Int. Cl.
*C07H 15/00* (2006.01)
*C07H 17/00* (2006.01)
*C07H 1/00* (2006.01)
*C07H 3/00* (2006.01)
*C07G 3/00* (2006.01)
*C08B 37/00* (2006.01)

(52) U.S. Cl. ...... 536/124; 536/18.4; 536/18.5; 536/18.6

(58) Field of Classification Search .................. 536/18.4, 536/18.5, 18.6, 124
See application file for complete search history.

(56) References Cited

FOREIGN PATENT DOCUMENTS

| | | |
|---|---|---|
| JP | 2001-172250 | 6/2001 |
| KR | 1020030038220 | 5/2003 |
| KR | 1020040006826 | 1/2004 |
| KR | 1020060122752 | 12/2006 |
| WO | WO 9831697 | 7/1998 |
| WO | WO 9839347 | 9/1998 |
| WO | WO 9961583 | 12/1999 |
| WO | WO 0114395 | 3/2001 |

OTHER PUBLICATIONS

Jung, ME et al., Efficient Synthesis of 2-Deoxy L-Ribose from L-Arabinose: Mechanistic Information on the 1,2-Acyloxy Shift in Alkyl Radicals. Organic Letters 1999, 1:1517-1519.
Kim, SK et al., Efficient Synthesis of 2-Deoxy-L-Ribose Starting from L-Ascorbic Acid. Journal of the Korean Chemical Society 1994, 38:783-784.
Stewart, AJ et al., 2-Deoxy-L-ribose from an L-arabinono-1,5-lactone. Tetrahedron: Asymmetry 2002, 13:2667-2672.
Urata, H et al., Synthesis and properties of mirror-image DNA. Nucleic Acids Research 1992, 20:3325-3332.

*Primary Examiner* — Layla Bland
(74) *Attorney, Agent, or Firm* — Henry D. Coleman; R. Neil Sudol; William J. Sapone

(57) ABSTRACT

A method of preparing 2-deoxy-L-ribose represented by the following formula I is disclosed. The preparation method includes the steps of: treating L-arabinose with an alcohol solvent in the presence of an acid to prepare 1-alkoxy-L-arabinopyranose; allowing the prepared 1-alkoxy-L-arabinopyranose to react with acyl chloride so as to prepare 1-alkoxy-2,3,4-triacyl-L-arabinopyranose; brominating the alkoxy group of the prepared 1-alkoxy-2,3,4-triacyl-L-arabinopyranose to prepare a 1-bromo-2,3,4-triacyl compound; allowing the prepared compound to react with zinc in the presence of ethyl acetate and an organic base so as to prepare glycal; treating the glycal with an alcohol solvent in the presence of an acid to prepare 1-alkoxy-2-deoxy-3,4-diacyl-L-ribopyranose; treating the prepared 1-alkoxy-2-deoxy-3,4-diacyl-L-ribopyranose with a base to prepare 1-alkoxy-2-deoxy-L-ribopyranose; and hydrolyzing the prepared 1-alkoxy-2-deoxy-L-ribopyranose in the presence of an acid catalyst.

19 Claims, 1 Drawing Sheet

PREPARATION METHOD OF 2-DEOXY-L-RIBOSE

TECHNICAL FIELD

The present invention relates to a method of preparing 2-deoxy-L-ribose of the following formula I, and more particularly to a method of preparing 2-deoxy-L-ribose in an industrially applicable and economic way:

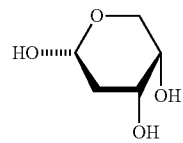

I

BACKGROUND ART

The literature relating to the prior art is as follows:
Korean Patent Registration No. 10-0433179;
Korean Patent Registration No. 10-0446560;
PCT International Patent Publication No. WO98/39347;
J. Korean Chem. Soc., 1994, 34, 783-784;
Nucleic Acids Res. 1992, 20, 3325-3332;
Org. Lett. 1999, 1, 1517-1519; and
Tetrahedron: Asymmetry 2002, 13, 2667-2672.

Recently, the L-isomers of natural or modified nucleosides have received attention as antiviral agents. L-thymidine, L-3'-thiacytidine (3TC), L-2',3'-dideoxycytidine (L-ddC) and the like exhibit remarkably low toxicity and good antiviral effects, compared to D-nucleosides. Also, L-nucleosides exhibit good effects in antisense oligonucleotide therapy. For this reason, many attempts have been made to effectively synthesize L-nucleosides which are not present in nature, and particularly, there have been studies focused on methods capable of economically producing a large amount of L-carbohydrates that are major intermediates of L-nucleosides, particularly 2-deoxy-L-ribose derivatives.

The prior art relating to the preparation of 2-deoxy-L-ribose will now be described.

A method of preparing 2-deoxy-L-ribose through the reduction and inversion reactions of an epoxy ring compound from D-arabinose as a starting material is known [Korean Patent Registration No. 10-0433179]. In this method, the selectivity in the reduction of the epoxy ring compound is problematic, and a lengthy process consisting of 10 steps should be carried out.

A method of preparing 2-deoxy-L-ribose through a six-step process from L-ribose is known [WO 98/39347, Tetrahedron Lett., 1997, 38, 4199-4202]. L-ribose and phenylselenol, used as main raw materials in this method, are expensive, and in addition, this method is not environment-friendly because tributyltin hydride has an unpleasant odor.

A method of preparing 2-deoxy-L-ribose from L-ascorbic acid via the intermediates 4-cyano-1,2-isopropylidene-1,2 (S),3(R)-butanetriol and 2-deoxy-L-ribose-1,5-lactone was reported [J. Korean Chem. Soc., 1994, 34, 783-784]. This method has disadvantages in that the preparation process is lengthy, and an expensive material such as diisoamylborane should be used as a reducing agent.

Various methods of preparing 2-deoxy-L-ribose using L-arabinose as a starting material, including a method of reducing the intermediate 2-(methylthio)thiocarbonyl activating functional group with tributyltin hydride, are known [Nucleic Acids Res. 1992, 20, 3325-3332, Org. Lett. 1999, 1, 1517-1519, Tetrahedron: Asymmetry 2002, 13, 2667-2672]. However, these methods are not suitable for the industrial mass production of 2-deoxy-L-ribose, because these methods employ highly toxic or expensive reagents and have low yield. In addition, a method of preparing 2-deoxy-L-ribose from 2-deoxy-D-ribose is known [Korean Patent Registration No. 10-0446560].

DISCLOSURE

Technical Problem

Accordingly, it is an object of the present invention to provide a method of preparing 2-deoxy-L-ribose in high yield in an industrially economical way as compared to the prior methods.

Technical Solution

To achieve the above object, according to one embodiment of the present invention, there is provided a method of preparing 2-deoxy-L-ribose of the following formula I, comprising the steps of: acylating and halogenating L-arabinose of the following formula (1) to prepare a 1-halo-2,3,4-triacyl compound of the following formula (5); allowing the compound of formula (5) to react with zinc in the presence of ethyl acetate and an organic base so as to prepare glycal of the following formula (6); treating the glycal of formula (6) with an alcohol solvent in the presence of an acid to prepare 1-alkoxy-2-deoxy-3,4-diacyl-L-ribopyranose of formula (7); treating the compound of formula (7) with a base to prepare 1-alkoxy-2-deoxy-L-ribopyranose of the following formula (8); and hydrolyzing the compound of formula (8) in the presence of an acid catalyst:

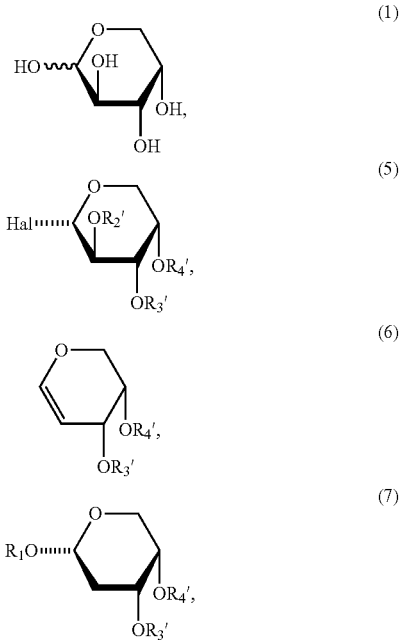

3
-continued

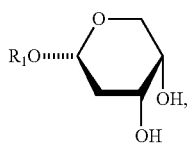
(8)

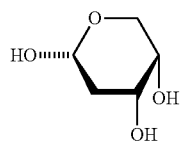
I wherein $R_1$ is an alkyl group, $R_2'$, $R_3'$, $R_4'$ are each an acyl group, and Hal is halogen.

According to another embodiment of the present invention, there is provided a method of preparing 2-deoxy-L-ribose of the following formula I, comprising the steps of: acylating and halogenating L-arabinose of the formula (1) to prepare a 1-halo-2,3,4-triacyl compound of the formula (5); allowing the compound of formula (5) to react with zinc in the presence of ethyl acetate and an organic base so as to prepare glycal of the formula (6); treating the glycal of formula (6) with sodium methoxide to prepare a compound of the following formula (10); and hydrolyzing the compound of formula (10) in the presence of an acid catalyst, and neutralizing the hydrolyzed compound with a base:

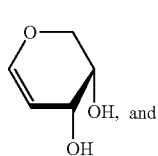
(10)

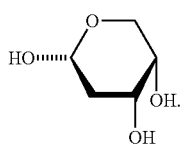
I

The step of acylating and halogenating L-arabinose of the formula (1) to prepare a 1-halo-2,3,4-triacyl compound of the formula (5) is carried out using one of two processes.

The first process comprises treating L-arabinose of the formula (1) with an alcohol solvent in the presence of an acid to prepare 1-alkoxy-L-arabinopyranose of the following formula (2), acylating the compound of formula (2) to 1-alkoxy-2,3,4-triacyl-L-arabinopyranose of the following formula (3), and halogenating the compound of formula (3):

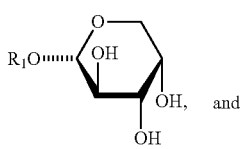
(2)

4
-continued

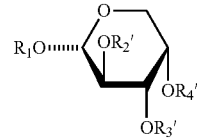
(3)

wherein $R_1$ is an alkyl group, and $R_2'$, $R_3'$ and $R_4'$ are each an acyl group.

The second process comprises acylating L-arabinose of the formula (1) to prepare 1,2,3,4-tetraacyl-L-arabinopyranose of the following formula (4), and halogenating the compound of formula (4):

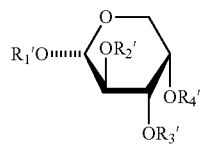
(4)

wherein $R_1'$, $R_2'$, $R_3'$ and $R_4'$ are each an acyl group.

Hereinafter, each step of the preparation method according to the present invention will be described.

I. Step of preparing 1-halo-2,3,4-triacyl compound

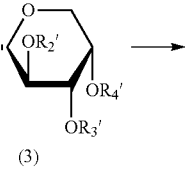

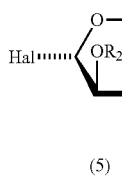
(5)

wherein $R_1$ is an alkyl group, $R_2'$, $R_3'$ and $R_4'$ are each an acyl group, and Hal is halogen.

In this step, L-arabinose is treated with an alcohol solvent in the presence of an acid and neutralized with an organic base, thus preparing 1-alkoxy-L-arabinopyranose represented by the formula (2). The acid that is used in this step is hydrogen chloride gas or acetyl chloride, and preferably one equivalent of acetyl chloride. The alcohol that is used in this step is a lower alkyl alcohol, in which $R_1$ is a $C_1$-$C_5$ lower alkyl group, preferably a C3-C4 alkyl group, and more preferably a primary propyl group. The organic base that is used in the neutralization is pyridine or triethylamine, with pyridine being preferred. The compound of formula (2) is allowed to react with 3-5 equivalents of acyl chloride in a pyridine solvent to quantitatively prepare 1-alkoxy-2,3,4-triacyl-L-arabinopyranose represented by the formula (3). Preferably, 3.6 equivalents of acyl chloride is used, and $R_2'$, $R_3'$ and $R_4'$ are preferably a benzoyl group or a toluoyl group, and more preferably a benzoyl group. The compound of formula (3) is allowed to react with 2-4 equivalents of a 30-33% halogen acid/acetic acid solution to quantitatively prepare the 1-halo-2,3,4-triacyl compound represented by the formula (5). Herein, 3 equivalents of a 30-33% hydrogen bromide/acetic acid solution is preferably used.

Another method of preparing the compound of formula (5) is as follows:

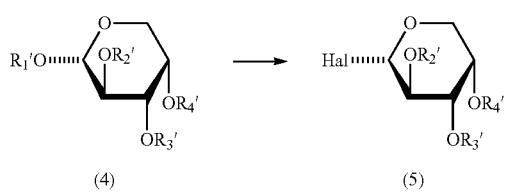

wherein $R_1'$, $R_2'$, $R_3'$ and $R_4'$ are each an acyl group, and Hal is halogen.

L-arabinose is allowed to react with 4-7 equivalents of acyl chloride in a pyridine solvent at room temperature to quantitatively prepare 1,2,3,4-tetraacyl-L-arabinopyranose represented by the formula (4), in which $R_1'$, $R_2'$, $R_3'$ and $R_4'$ are each preferably a benzoyl group or a toluoyl group, and more preferably a benzoyl group. The compound of formula (4) is allowed to react with 1-4 equivalents of a 30-33% halogen acid/acetic acid solution to quantitatively prepare the 1-halo-2,3,4-triacyl compound represented by the formula (5). Herein, 2 equivalents of a 30-33% hydrogen bromide/acetic acid solution is preferably used. Although the use of a 1-bromo-triacetyl compound as an intermediate was reported [*Nucleoside, Nucleotide & Nucleic Acids,* 2002, 21, 155-163, *J. Am. Chem. Soc.* 2002, 124, 6576-6583, *Bioorg. & Med. Chem.* 2004, 12, 1781-1791.], this compound is not industrially useful, because it is prepared in a yield of less than 60% and is unstable. However, in the present invention, the 1-bromo-2,3,4-tribenzoyl compound can be prepared in high yield and is stable and industrially useful.

II. Step of preparing glycal

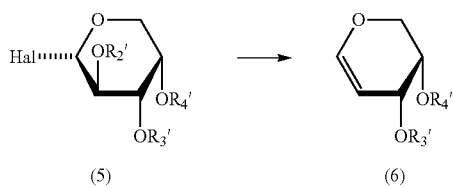

wherein $R_2'$, $R_3'$ and $R_4'$ are each an acyl group, and Hal is halogen.

In this step, the compound of formula (5) is allowed to react with 5-15 equivalents of zinc in the presence of ethyl acetate and 0.5-2 equivalents of an organic base so as to quantitatively prepare glycal of the formula (6). The organic base that is used in this step is 1.05 equivalents of N-methylimidazole, pyridine or triethylamine, and preferably 1.05 equivalents of N-methylimidazole. Preferably, 10 equivalents of zinc is used. After completion of the reaction, the reaction product is added to an excess of ethyl acetate, neutralized with 2M sulfuric acid, washed three times with saturated sodium bicarbonate, dried with sodium sulfate, concentrated, and then used in the next step without requiring any purification process.

III. Step of preparing 2-deoxy-L-ribose

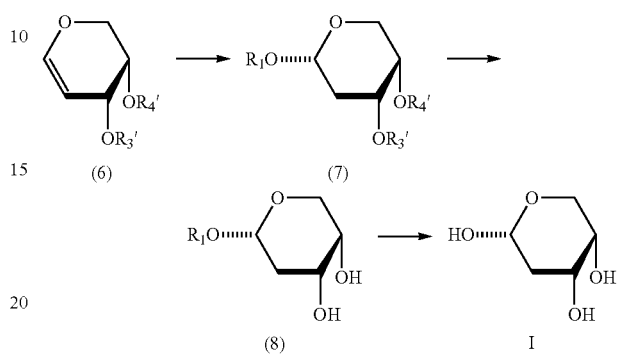

wherein $R_1$ is an alkyl group, and $R_3'$ and $R_4'$ are each an acyl group.

In this step, the compound of formula (6) is treated with an alcohol solvent in the presence of an acid and neutralized with an organic base, thus preparing 1-alkoxy-2-deoxy-3,4-diacyl-L-ribopyranose represented by the formula (7). The acid that is used in this step is hydrogen chloride gas or acetyl chloride, and preferably 0.5-3 equivalents of acetyl chloride. More preferably, 1.5 equivalents of acetyl chloride is used as the acid. The alcohol that is used in this step is a lower alkyl alcohol, in which $R_1$ is a $C_1$-$C_5$ lower alkyl group, preferably a $C_3$-$C_4$ alkyl group, and more preferably a tertiary-butyl group. The organic base that is used in the neutralization is pyridine or triethylamine, and preferably triethylamine. Then, the compound of formula (7) is allowed to react with 0.3-1 equivalent of a base in a methanol solvent so as to quantitatively prepare 1-alkoxy-2-deoxy-L-ribose represented by the formula (8). The base that is used in the reaction is sodium hydroxide or sodium methoxide.

Then, the compound of formula (8) is hydrolyzed in the presence of a dilute acid catalyst at 40° C. for 5 hours, and then concentrated, thus preparing 2-deoxy-L-ribose of formula I in high yield. As the acid, an inorganic acid or an organic acid may be used. Preferably, the inorganic acid is a dilute sulfuric acid or a dilute hydrochloric acid, and the organic acid is a dilute acetic acid. More preferably, 1-10% acetic acid is used. In order to purify 2-deoxy-L-ribose of formula I, prepared according to the above method, the compound of formula I is added to isopropanol, aniline is added thereto, and the solution is crystallized from methanol, thus preparing L-anilide represented by formula (9) below. Particularly, the compound of formula (9) is advantageous for long-term storage, because it is very stable.

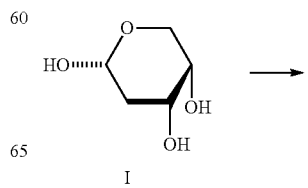

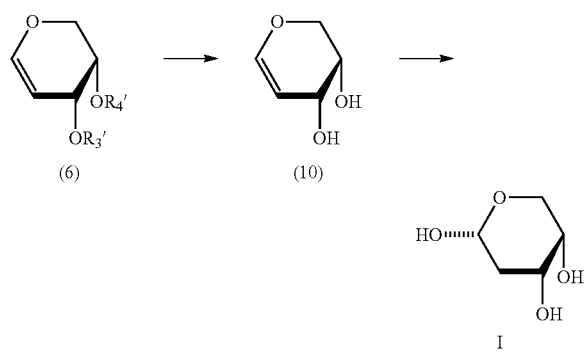

Another method of preparing the compound of formula I is as follows:

Example 1

Preparation of 1-propoxy-L-arabinopyranose 3.917 kg (65 mol) of 1-propanol was placed in a reactor, and the temperature within the reactor was lowered to a temperature between −10° C. to 10° C. Then, 0.523 kg (6.7 mol) of acetyl chloride was added slowly thereto at a temperature between −10° C. to 35° C. To the solution, 1 kg (6.7 mol) of L-arabinose was added, and the mixture was warmed to 35-40° C. and stirred at that temperature for 2-3 hours, and then at 27-32° C. for 20 hours. After completion of the reaction, the solids were filtered and washed with 0.536 kg of 1-propanol. The filtered solids and 3.6 liters of dichloromethane were placed in a reactor and stirred for 1-2 hours. After this, 0.079 kg of pyridine was added thereto, and the mixture was stirred for 30 minutes, filtered, washed with 0.662 liters of dichloromethane, and then dried in a vacuum, thus obtaining 1.024 kg (80% yield) of 1-propoxy-L-arabinose. $^1$H NMR ($D_2O$): δ 4.85 (d, 1H), 3.90 (m, 1H), 3.85-3.65 (m, 3H), 3.55 (m, 2H), 3.40 (m, 1H), 1.55 (m, 2H), 0.85 (t, 3H).

The compound of formula (6) is dissolved in methanol and treated with 0.2-1 equivalent of sodium methoxide, thus preparing the compound of formula (10). Preferably, 0.5 equivalents of sodium methoxide are used. Then, the compound of formula (10) is hydrolyzed in the presence of an acid catalyst at 0° C. for 4 hours, and then neutralized with a base, thus preparing 2-deoxy-L-ribose of formula I in high yield. As the acid, an inorganic acid or an organic acid may be used. Preferably, the inorganic acid is a dilute sulfuric acid or a dilute hydrochloric acid, and the organic acid is acetic acid. More preferably, 2.5% sulfuric acid is used. As the base, sodium hydroxide is used.

In the same manner as in the first method, the prepared 2-deoxy-L-ribose is added to isopropanol, aniline is added thereto, and the solution is crystallized from methanol, thus preparing L-anilide represented by the formula (9).

A preferred embodiment of the present invention is shown in FIG. 1.

As shown in FIG. 1, the preparation of the 1-halo-2,3,4-triacyl compound represented by the formula (5) is carried out according to one of two processes, and the preparation of 2-deoxy-L-ribose from the glycal of formula (6) is also carried out according to one of two processes. The most preferred processes are the processes shown on the left side of FIG. 1, and a benzoyl group is most preferably used as the acyl group. In FIG. 1, Bz represents a benzoyl group, Pr represents a propyl group, and t-Bu is a tertiary-butyl group.

Example 2

Preparation of 1-propoxy-2,3,4-tribenzoyl-L-arabinopyranose 2.88 kg of pyridine and 1 kg (5.20 mol) of 1-propoxy-L-arabinopyranose were placed in a reactor, stirred for 30 minutes and then cooled to a temperature between −15° C. and 5° C. 2.633 kg (18.7 mol) of benzoyl chloride was added dropwise thereto, and the mixture was stirred at 35-45° C. for 2 hours, and then stirred with 1.15 liters of ethyl acetate at the same temperature for 1 hour. After completion of the reaction, the reaction solution was cooled to room temperature, 0.34 liters of methanol was added thereto, and the solution was stirred for 30 minutes. The stirred solution was added to 0.52 liters of purified water and completely concentrated at a temperature lower than 50° C. To the concentrate, 6.05 liters of toluene and 0.52 liters of purified water were added, and the solution was stirred, and then separated into layers. The organic layer was washed with 2.6 liters of dilute sulfuric acid, 1.6 liters of aqueous saturated sodium chloride solution, 1.6 liters of aqueous saturated sodium bicarbonate solution and 1.6 liters of aqueous saturated sodium chloride solution, and the oil layer was dried with sodium sulfate, and then concentrated, thus obtaining 2.622 kg (100% yield) of 1-propoxy-2,3,4-tribenzoyl-L-arabinopyranose.

BEST MODE

Figure 1:
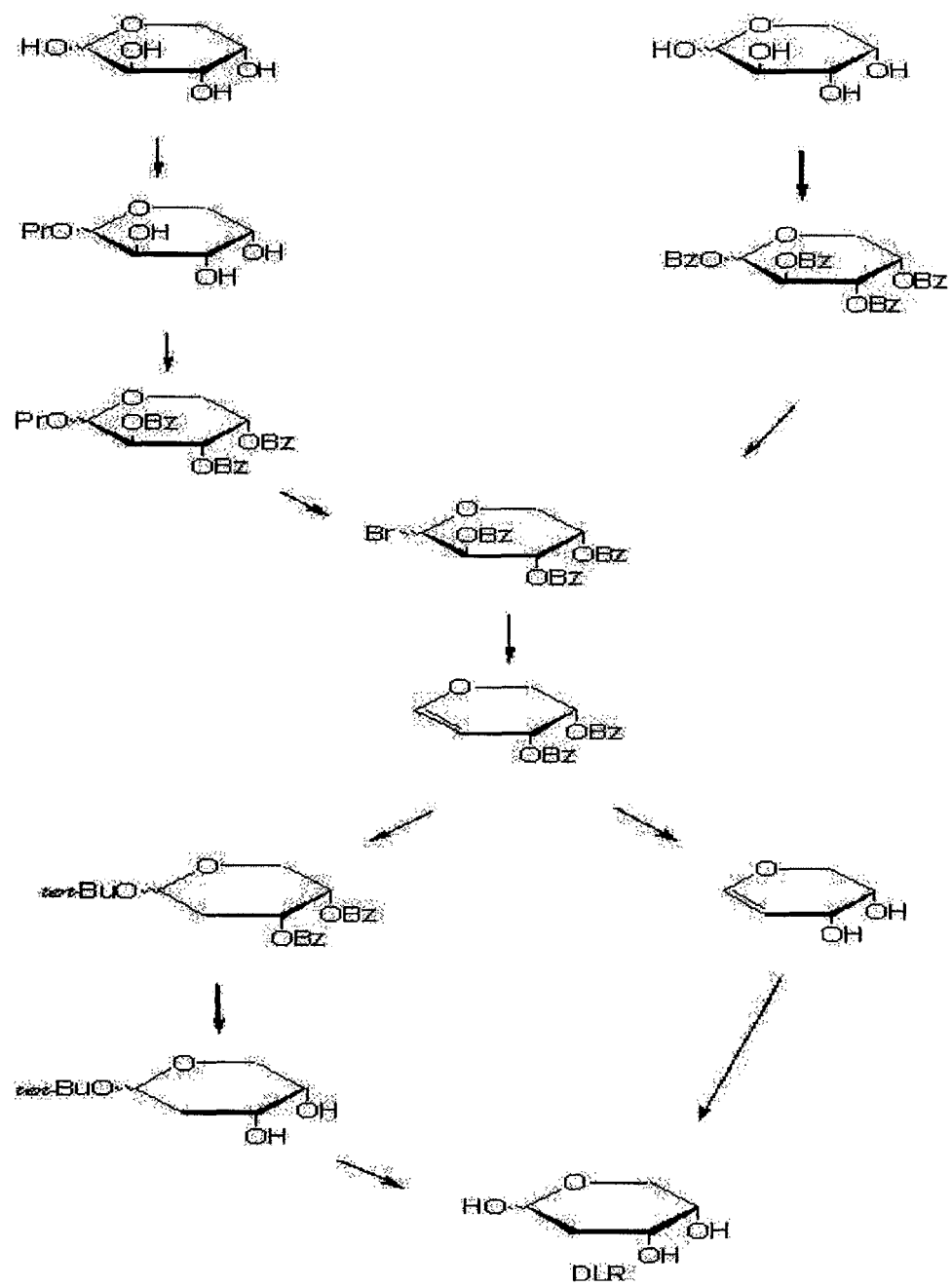
FIG. 1 is a schematic diagram showing an embodiment of the present invention.

Hereinafter, the present invention will be described in further detail with reference to the following examples. It is to be understood, however, that these examples are illustrative only and the present invention is not limited thereto.

Example 3

Preparation of 1,2,3,4-tetrabenzoyl-L-arabinopyranose 1 kg (6.7 mol) of L-arabinose was added to 4 liters of pyridine and cooled to a temperature of 0° C., and then 5.34 kg (38.0 mol) of benzoyl chloride was slowly added dropwise thereto. The reaction mixture was stirred at room temperature for 5 hours, the pyridine was removed by concentration, 3.3 liters of toluene was added to the residue, and the solution was azeotropically distilled with 3.3 liters of toluene. 6.7 liters of ethyl acetate was added to the resulting material, which was then washed two times with 6.7 liters of water, and the oil layer was dried with sodium sulfate, and then concentrated, thus quantitatively obtaining 1,2,3,4-tetrabenzoyl-L-arabinopyranose. $^1$H NMR (CDCl$_3$): δ 8.20-7.25 (m, 20H), 6.25 (d, 1H), 5.95 (t, 1H), 5.75 (m, 2H), 4.45 (dd, 1H), 4.15 (dd, 1H).

Example 4

Preparation of 1-bromo-2,3,4-tribenzoyl-L-arabinopyranose

While the internal temperature of the reactor containing 2.622 kg (5.20 mol) of 1-propoxy-2,3,4-tribenzoyl-L-arabinopyranose was maintained at 0-20° C., 4.21 kg of a 30-33% hydrogen bromide/acetic acid solution was added dropwise thereto, and the mixture was stirred at room temperature for 6 hours. After completion of the reaction, 1.296 liters of dichloromethane was added to the reaction solution, which was then stirred for 30 minutes. The stirred solution was added dropwise to a reactor containing 4.162 liters of purified water and stirred for 30 minutes. Then, the stirred solution was separated into layers. The water layer was back-extracted with 1.296 liters of dichloromethane. The oil layer was washed two times with 0.195 kg of aqueous saturated sodium chloride solution and one time with 0.248 kg of aqueous saturated sodium bicarbonate solution, and then dried with sodium sulfate, and the solvent was removed by concentration. To the concentrated residue, 1.30 liters of dichloromethane was added, and the solution was stirred for 2-3 hours. 6.50 liters of hexane was added to the stirred solution, which was then cooled to a temperature of 0-5° C., stirred for 3-4 hours, and filtered. The filtered solids were washed with 2.76 liters of hexane and dried in a vacuum, thus obtaining 2.185 kg (80% yield) of 1-bromo-2,3,4-tribenzoyl-L-arabinopyranose. $^1$H NMR (CDCl$_3$): δ 8.20-7.90 (dd, 4H), 7.90-7.80 (d, 2H), 7.70-7.20 (m, 9H), 6.93 (d, 1H), 5.97 (dd, 1H), 5.82 (m, 1H), 5.70 (dd, 1H), 4.50 (d, 1H), 4.25 (d, 1H).

Example 5

Preparation of 1-bromo-2,3,4-tribenzoyl-L-arabinopyranose

While the internal temperature of the reactor containing 2.946 kg (5.20 mol) of 1,2,3,4-tetrabenzoyl-L-arabinopyranose was maintained at 0-20° C., 4.21 kg of a 30-33% hydrogen bromide/acetic acid solution was added dropwise thereto, and the mixture was stirred at room temperature for 6 hours. After completion of the reaction, 1.296 liters of dichloromethane was added to the reaction solution, which was then stirred for 30 minutes. Next, the solution was added dropwise to a reactor containing 4.162 liters of purified water, and was stirred for 30 minutes, and then separated into layers. The water layer was back-extracted with 1.296 liters of dichloromethane. The oil layer was washed two times with 0.195 kg of aqueous saturated sodium chloride solution and one time with 0.248 kg of aqueous saturated sodium bicarbonate solution, and then dried with sodium sulfate, and the solvent was removed by concentration. To the concentrated residue, 1.30 liters of dichloromethane was added, the solution was stirred for 2-3 hours, and 6.50 liters of hexane was added thereto. The resulting solution was cooled to 0-5° C., stirred for 3-4 hours, and then filtered. The filtered solids were washed with 2.76 liters of hexane and dried in a vacuum, thus obtaining 1.912 kg (70% yield) of 1-bromo-2,3,4-tribenzoyl-L-arabinopyranose. $^1$H NMR (CDCl$_3$): δ 8.20~7.90 (dd, 4H), 7.90~7.80 (d, 2H), 7.70~7.20 (m, 9H), 6.93 (d, 1H), 5.97 (dd, 1H), 5.82 (m, 1H), 5.70 (dd, 1H), 4.50 (d, 1H), 4.25 (d, 1H).

Example 6

Preparation of 3,4-dibenzoyl-glycal

To a reactor, 1.245 kg (19.04 mol) of zinc, 0.164 kg (2.00 mol) of N-methylimidazole and 1.24 liters of ethyl acetate were added, and the contents of the reactor were refluxed at a temperature of 75-83° C. To another reactor, 1 kg (1.9 mol) of 1-bromo-2,3,4-tribenzoyl-L-arabinopyranose and 1.62 liters of ethyl acetate were added, and the contents of the reactor were sufficiently dissolved, and then added dropwise to the refluxing reactor over 3-5 hours. Then, the solution was refluxed for 30 minutes. After completion of the reaction, the reaction solution was cooled, the zinc was filtered out, the residue was washed with 0.66 liters of ethyl acetate, and the organic layer was completely concentrated and was dissolved in 1.542 liters of ethyl acetate. The resulting material was washed two times with 1.05 liters of 2M sulfuric acid solution, two times with 1 liter of aqueous saturated sodium chloride solution and two times with 1 liter of aqueous saturated sodium bicarbonate solution, and then dried with sodium sulfate, and the solvent was removed by concentration, thus obtaining 0.62 kg (100% yield) of 3,4-dibenzoyl-glycal. $^1$H NMR (CDCl$_3$): δ 8.10-7.90 (dd, 4H), 7.70-7.30 (d, 6H), 6.62 (d, 1H), 5.82 (t, 1H), 5.55 (m, 1H), 5.10 (t, 1H), 4.25 (m, 2H).

Example 7

Preparation of 1-t-butoxy-2-deoxy-3,4-dibenzoyl-L-ribose

A solution of 0.205 kg (2.61 mol) of acetyl chloride in 4.756 kg of t-butanol was slowly added dropwise to the reactor containing 0.62 kg (1.9 mol) of 3,4-dibenzoyl-glycal, and the contents of the reactor were stirred for 10 hours. After completion of the reaction, 0.276 kg of triethylamine was added to the reaction solution, which was then completely concentrated. To the concentrated residue, 3.16 liters of ethyl acetate was added, and the solution was washed two times with 2.65 liters of purified water, and then concentrated, thus obtaining 0.61 kg (80% yield) of 1-t-butoxy-2-deoxy-3,4-dibenzoyl-L-ribose.

$^1$H NMR (CDCl$_3$): δ 8.20-7.10 (m, 10H), 5.75 (m, 1H), 5.55 (m, 1H), 5.37 (m, 1H), 2.5-1.9 (m, 2H), 1.3 (s, 9H).

Example 8

Preparation of 1-t-butoxy-2-deoxy-L-ribose 0.61 kg (1.53 mol) of 1-t-butoxy-2-deoxy-3,4-dibenzoyl-L-ribose was dissolved in 6.02 liters of methanol for 30 minutes, and 0.041 kg of 25 w % sodium methoxide methanol solution was added thereto. The mixture solution was stirred at room temperature at room temperature. After completion of the reaction, 0.013 kg of ammonium chloride was added to the reaction solution, which was then stirred for 2 hours, and 0.038 kg of celite was added thereto. Next, the solution was stirred for 30 minutes, and then concentrated. To the concentrated residue, 2.531 liters of ethyl acetate was added at 35-45° C., and the solution was stirred at the same temperature for 2-3 hours. The stirred solution was filtered using 0.038 kg of celite, and was washed with 0.422 liters of ethyl acetate, and then completely concentrated, thus obtaining 0.29 kg (100% yield) of 1-t-butoxy-2-deoxy-L-ribose.

Example 9

Preparation of 2-deoxy-L-ribose 0.5 kg (2.63 mol) of 1-t-butoxy-2-deoxy-L-ribose was dissolved in 2 liters of 1% acetic acid, and stirred at 40° C. for 5 hours. After completion of the reaction, the solvent was removed by concentration, and the residue was azeotropically distilled with toluene, thus obtaining 2-deoxy-L-ribose, which was then used for the preparation of L-anilide without any purification.

Example 10

Preparation of L-Anilide

The concentrated residue of Example 9 was added and well dissolved in 2.5 liters of isopropanol with stirring for 1 hour. Then, 0.24 kg of aniline was added thereto, and the mixture was stirred at room temperature for 1 hour. As solids were formed, the solution was cooled to 10-20° C., stirred for 2 hours, and filtered. The filtered solids were washed with isopropanol and hexane and dried, thus 0.44 kg (80% yield) of L-anilide.

Example 11

Preparation of 2-deoxy-L-ribose 30.7 g (0.095 mol) of 3,4-dibenzoyl-glycal was dissolved in 150 ml of methanol, and 2.6 g (0.047 mol) of sodium methoxide was added thereto. The mixture solution was stirred for 3 hours, neutralized with acetic acid, concentrated, and then azeotropically distilled with 100 ml of toluene. The concentrated residue was added to 10 ml of 2.5% sulfuric acid at 0° C., and then stirred for 5 hours, while the reaction temperature was elevated slowly to room temperature. Then, the temperature was lowered to 0° C., and the reaction solution was neutralized by slow dropwise addition of 3.5% aqueous sodium hydroxide solution, and azeotropically distilled with 30 ml of ethanol. The distilled material was stirred with 30 ml of ethanol at 60-70° C. and filtered to remove inorganic salts. The residue was washed with 20 ml of ethanol and concentrated, thus obtaining 8.9 g (70% yield) of 2-deoxy-L-ribose. The product was subjected to the same process as described in Example 10, thus preparing L-anilide.

INDUSTRIAL APPLICABILITY

As can be seen from the foregoing, according to the preparation method of the present invention, a large amount of 2-deoxy-L-ribose can be easily produced in high yield. Accordingly, the method of the present invention is highly effective in industrially producing 2-deoxy-L-ribose, compared to the prior methods.

The invention claimed is:

1. A method of preparing 2-deoxy-L-ribose of the following formula I, comprising the steps of: acylating and halogenating L-arabinose of the following formula (1) to prepare a 1-halo-2,3,4-triacyl compound of the following formula (5); allowing the compound of formula (5) to react with zinc in the presence of ethyl acetate and an organic base so as to prepare glycal of the following formula (6); treating the glycal of formula (6) with an alcohol solvent in the presence of an acid to prepare 1-alkoxy-2-deoxy-3,4-diacyl-L-ribopyranose of formula (7); treating the compound of formula (7) with a base to prepare 1-alkoxy-2-deoxy-L-ribopyranose of the following formula (8); and hydrolyzing the compound of formula (8) in the presence of an acid catalyst:

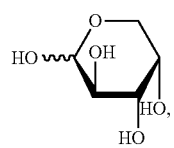

(1)

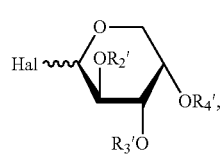

(5)

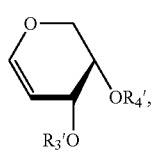

(6)

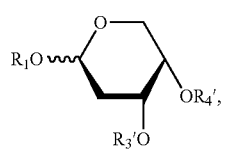

(7)

(8)

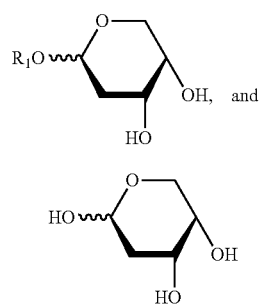

I wherein $R_1$ is a $C_1$-$C_5$ alkyl group, $R_2'$, $R_3'$, $R_4'$ are each benzoyl or toluyl, and Hal is halogen.

2. The method of claim 1, wherein the step of acylating and halogenating L-arabinose of the formula (1) to prepare the 1-halo-2,3,4-triacyl compound of formula (5) comprises treating L-arabinose of the formula (1) with an alcohol solvent in the presence of an acid to prepare 1-alkoxy-L-arabinopyranose of the following formula (2), acylating the compound of formula (2) to prepare 1-alkoxy-2,3,4-triacyl-L-arabinopyranose of the following formula (3), and halogenating the compound of formula (3) to obtain the 1-halo-2,3,4-triacyl compound of formula (5):

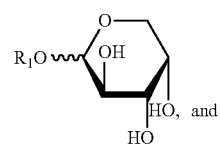

(3)

(4)

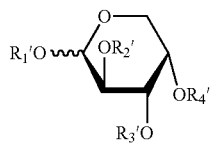

wherein $R_1$ is a lower alkyl group, and $R_2'$, $R_3'$ and $R_4'$ are each benzoyl or toluyl.

3. The method of claim 1, wherein the step of acylating and halogenating L-arabinose of the formula (1) to prepare the 1-halo-2,3,4-triacyl compound of formula (5) comprises acylating L-arabinose of the formula (1) to prepare 1,2,3,4-tetraacyl-L-arabinopyranose of the following formula (4):

(4)

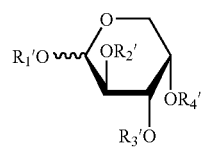

wherein $R_1'$, $R_2'$, $R_3'$ and $R_4'$ are each benzoyl or toluyl, and halogenating the compound of formula (4) to obtain the 1-halo-2,3,4-triacyl compound of formula (5).

4. The method of claim 3, wherein $R_1'$, $R_2'$, $R_3'$ and $R_4'$ are each benzoyl, and Hal is bromine.

5. The method of claim 2, wherein the acylation is carried out using acyl chloride in a pyridine solvent.

6. The method of claim 2 wherein the halogenation is carried out using hydrogen bromide.

7. The method of claim 1, wherein the organic base that is used in the preparation of the glycal is one selected from the group consisting of N-methylimidazole, pyridine, triethylamine, and mixtures thereof.

8. The method of claim 1, wherein the base that is used for treating 1-alkoxy-2-deoxy-3,4-diacyl-L-ribopyranose of formula (7) is sodium hydroxide or sodium methoxide.

9. The method of claim 1, wherein the acid catalyst that is used in the hydrolysis is a dilute sulfuric acid, a dilute hydrochloric acid or a dilute acetic acid, and the hydrolysis is carried out at 40° C.

10. A method of preparing 2-deoxy-L-ribose of the following formula I, comprising the steps of: acylating and halogenating L-arabinose of the following formula (1) to a 1-halo-2,3,4-triacyl compound of the following formula (5); allowing the compound of formula (5) to react with zinc in the presence of ethyl acetate and an organic base so as to prepare glycal of the following formula (6); and treating the compound of formula (6) with sodium methoxide to prepare a compound of the following formula (10), hydrolyzing the compound of formula (10) in the presence of an acid catalyst, and neutralizing the hydrolyzed compound with a base:

(1)

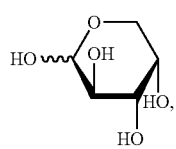

(5)

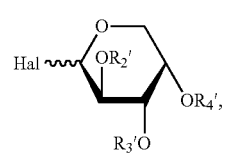

(6)

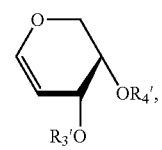

(10)

I

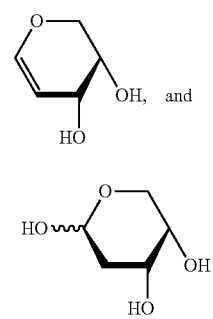

wherein $R_2'$, $R_3'$, $R_4'$ are each an acyl group, and Hal is halogen.

11. The method of claim 10, wherein the step of acylating and halogenating L-arabinose of the formula (1) to prepare the 1-halo-2,3,4-triacyl compound of formula (5) comprises treating L-arabinose of the formula (1) with an alcohol solvent in the presence of an acid to prepare 1-alkoxy-L-arabinopyranose of the following formula (2), acylating the compound of formula (2) to prepare 1-alkoxy-2,3,4-triacyl-L-arabinopyranose of the following formula (3), and halogenating the compound of formula (3) to obtain the 1-halo-2,3,4-triacyl compound of formula (5):

(2)

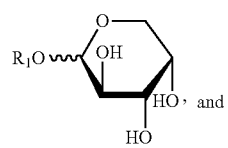

(3)

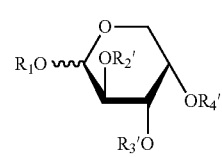

wherein $R_1$ is a lower alkyl group, and $R_2'$, $R_3'$ and $R_4'$ are each an acyl group.

12. The method of claim 10, wherein the step of acylating and halogenating L-arabinose of the formula (1) to prepare the 1-halo-2,3,4-triacyl compound of formula (5) comprises acylating L-arabinose of the formula (1) to prepare 1,2,3,4-tetraacyl-L-arabinopyranose of the following formula (4):

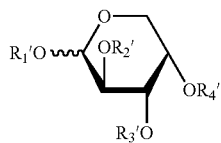

(4)

wherein $R_{1'}$, $R_{2'}$, $R_{3'}$ and $R_{4'}$ are each an acyl group, and halogenating the compound of formula (4) to obtain the 1-halo-2,3,4-triacyl compound of formula (5).

13. The method of claim 10, wherein $R_1$ is a $C_1$-$C_5$ lower alkyl group, $R_2'$, $R_3'$ and $R_4'$ are each benzoyl or toluyl, and Hal is bromine.

14. The method of claim 12, wherein $R_1'$, $R_2'$, $R_3'$ and $R_4'$ are each benzoyl or toluyl, and Hal is bromine.

15. The method of claim 11, wherein the acylation is carried out by allowing the compound of formula (2) to react with acyl chloride in a pyridine solvent.

16. The method of claim 11, wherein halogenation is carried out using hydrogen bromide.

17. The method of claim 10, wherein the organic base that is used in the preparation of the glycal is one selected from the group consisting of N-methylimidazole, pyridine, triethylamine, and mixtures thereof.

18. The method of claim 10, wherein the acid catalyst that is used in the hydrolysis is a dilute sulfuric acid, a dilute hydrochloric acid or a dilute acetic acid, and the hydrolysis is carried out at 0° C.

19. The method of claim 12, wherein the acylation is carried out by allowing the compound of formula (1) to react with acyl chloride in a pyridine solvent.

* * * * *